United States Patent [19]

Halcomb, III et al.

[11] Patent Number: 4,517,969
[45] Date of Patent: May 21, 1985

[54] PROSTHETIC GAUGE

[75] Inventors: F. Joseph Halcomb, III, Warsaw, Ind.; C. Wayne Allen, Memphis, Tenn.

[73] Assignee: Zimmer, Inc., Warsaw, Ind.

[21] Appl. No.: 471,967

[22] Filed: Mar. 3, 1983

[51] Int. Cl.³ .............................................. A61F 5/04
[52] U.S. Cl. .................................. 128/92 E; 33/512; 128/303 R
[58] Field of Search ........................ 33/174 D, 178 B; 128/92 R, 303 R, 92 E

[56] References Cited

U.S. PATENT DOCUMENTS 3,658,421   4/1982   Shelton ............................ 33/178 B
4,211,241   7/1980   Kaster et al. .................... 33/174 D

OTHER PUBLICATIONS

W. H. Harris, P. D. Rushfeldt, C. E. Carlson, J. M. Scholler, R. W. Mann, "Pressure Distribution in the Hip and Selection of Hemiarthroplasty", *The Hip: Proceedings of the Third Open Scientific Meeting of the Hip Society*, 1975, pp. 93–98.
Howmedica, Inc.—Catalog p. A-34, Harris Femoral Head Gauge, Product No. 6791-7-000, ©, 1978.
Zimmer, Inc.—Catalog p. A-61—STH ™ Acetabular Gauge Set, Product #4048-25, 29, (1981).
Zimmer, Inc.—Catalog p. A-70, Charnley Acetabular Gauge, Product #4033-28, (1981).
Zimmer, Inc.—Catalog p. A-78, Contour Gauges 5035-49, 50 and Acetabular Shell Gauges 5035-35, (1981).
Zimmer, Inc.—Catalog pp. A-79 and A-76, Femoral Template Set 5035-51, (1981).
Zimmer, Inc.—Catalog p. A-84, Giliberty ® II Provisional (Trial), Endoprostheses, 5068-12/27, (1981).
Halcomb, F. J., R. W. Mann and W. H. Harris, 1982, "In Vivo Pressure Distribution Measurements in the Human Acetabulum and Selection of Endoprosthesis Size", Abstract—Third Meeting of the European Society of Biomechanics (Sint Radboudziekenhuis University of Nijmegan, The Netherlands).
Rushfeldt, P. D., C. E. Carlson, R. W. Mann, and W. H. Harris, "Load Distribution Across Human Acetabular Cartilage: In Vivo Studies Using and Instrumented Femoral Head Prosthesis", *Journal of Bone and Joint Surgery*, vol. 57-A, No. 4, Jun. 1975, p. 565.
Rushfeldt, P. D., R. W. Mann, W. H. Harris, "Effect of Incongruity in Hemiarthroplasty on Pressures and Torques in the Hip Joint", 28th Annual Conference of Engineering in Medicine and Biology (ACEMB), New Orleans, LA, 1975, p. 145.
Willen Bros. Ltd., London, England, "Crawford Adams Spherical Cups & Acetabulum Gauge", date unknown.

*Primary Examiner*—C. Fred Rosenbaum
*Assistant Examiner*—C. W. Shedd
*Attorney, Agent, or Firm*—Margaret L. Geringer

[57] ABSTRACT

A prosthetic gauge which is used for evaluating the fit of a prosthetic device against a receiving bone or cartilage surface. The gauge includes a portion for gripping and a contact portion extending from the gripping portion. The surface of the contact portion is predeterminedly contoured to conform substantially to the shape of the receiving bone or cartilage surface to be evaluated. The contact surface is a frosted or translucent surface which transmits and diffuses light so that the specific bone or cartilage surface being observed through the gauge cannot be seen clearly until actual contact is made between the contact surface and the articular surface. This aids the surgeon in more accurately determining the apparent contact area, and hence in evaluating the potential fit of the prosthesis.

9 Claims, 6 Drawing Figures

PROSTHETIC GAUGE

BACKGROUND OF THE INVENTION

The present invention generally relates to gauges, and more particularly, to prosthetic gauges used for evaluating the fit of a prosthetic implant prior to operative reconstruction of a joint.

Orthopaedic surgeons frequently find it nesessary to utilize a gauge to select the proper size of prosthetic implant for replacement of a joint surface. Gauges can be adapted for use to select the proper size of prosthesis for many types of joint surfaces, such as the femoral head, the acetabulum, and the tibial surface of the knee. In the case of an endoprosthesis where an artificial ball joint surface is utilized to articulate against the natural acetabular cartilage, determination of the proper ball size to mate with the acetabulum is particularly important.

A variety of techniques have been used to select the proper size of endoprosthesis for a hemiarthroplasty. These current methods are often very subjective and can be misleading. Furthermore, these known techniques generally do not provide a means for assessing the contact areas between the prosthetic replacement and the acetabular articular cartilage.

The necessity and importance of proper prosthetic selection and the concept of optimal fit for an endoprosthesis is supported in Chapter 5, "Pressure Distribution in the Hip and Selection of Hemiarthroplasty," by W. H. Harris, P. D. Rushfeldt, C. E. Carlson, J. M. Scholler, and R. W. Mann in *THE HIP, Proceedings of the Third Open Scientific Meeting of the Hip Society*, 1975, pp. 93–98. This article indicates that poor fit of the ball of the endoprosthesis to the articular cartilage may lead to failure of the endoprosthesis. It indicates that "mismatches in either direction, that is, a prosthesis too large or too small for the socket, could make the local load on the acetabular cartilage higher, possibly even excessively high for cartilage survival." The authors indicate that proper prosthetic selection could improve the results from the use of endoprostheses and possibly improve the longevity of these implants.

The article also describes many of the techniques known for selecting the endoprosthesis size. One technique described as a method of size selection is the "shuck" test. The "shuck" test presumably means that a series of prostheses are tried in the acetabular socket, and the one with least "shuck" is selected. This method is very crude and subjective.

This same article states that "current clinical practice also involves some measurement with calipers, but at times these measurements may be inappropriate, inaccurate or even misleading." Calipers only provide a measurement in one arc and not the whole surface profile. The article also notes that the determination of prosthesis fit is frequently made on the basis of a feeling of suction between the socket and the prosthesis. This feeling of suction has been shown to have almost nothing to do with the fit of an endoprosthesis.

This article also illustrates and describes the use of transparent glass spheres which were used to study contact area between sphere and acetabular cartilage by direct visualization. The article indicates that the crux of the matter is to be able to determine the contact surface, that is, the area over which the prosthesis makes good contact with the socket. The transparent spheres were used so that one could see the contact profile by direct observation. However, the disadvantage of this technique is that all of the cartilage surface can be seen through the transparent spheres. Consequently, it is difficult to determine whether the cartilage surface is actually in contact with the sphere or just below the surface of the sphere, but still visible. It is also noted that glass spheres would not be desirable for use in an operative procedure for safety reasons, such as potential breakage.

A "go or no go" femoral head gauge is also disclosed in this same article. This template-type gauge is used to determine the diameter of the femoral head. The correct size of prosthesis to use is one whose diameter equals the smallest hole through which the femoral head will pass. However, the measurements obtained by the "go no go" gauge template provide no information about contact at the zenith of the acetabulum.

Proper contact between a prosthetic implant and its mating bone surface is also important when using prostheses which are adapted for bony ingrowth. Typically, prostheses adapted for bony ingrowth utilize a porous material on the prosthesis surface which will be in contact with the bone surface. Such bone ingrowth prostheses do not utilize bone cement on the bone ingrowth surface. This enables the bone to be in contact with this porous surface, so as to enable the bone to grow into the porous surface. For successful bone ingrowth, it is important that the bone be in good direct contact with the porous surface of the prosthesis. Thus, it is very important that there is proper fit and good contact area between the implant and its mating bone surface to achieve the best fit. One such porous material which is suitable for bony ingrowth is disclosed in U.S. Pat. No. 3,906,550 to Rostoker and Galante.

OBJECTS OF THE INVENTION

A principle object of this invention is to provide a prosthetic gauge which enhances visualization of the contact surface of bone or cartilage which will be receiving a prosthetic component, to aid in evaluating the fit of the prosthesis more accurately.

Another object of the invention is to provide a means of determining the apparent contact area between the prosthesis and the receiving cartilage or bone surface.

A further object of the invention when dealing with the acetabulum is to provide a means of determining both the diameter of the acetabulum and the apparent contact area between the prosthesis and acetabular cartilage.

A still further object of the invention is to provide a translucent surface on the contact surface of a prosthetic gauge so that the specific cartilage or bone surface being observed through the gauge cannot be seen clearly until actual contact is made between the gauge and the cartilage or bone surface.

A further object of the invention is to provide such prosthetic gauges in a number of different sizes to aid in the proper selection of a prosthesis for a given articular surface.

A further object of the invention is to provide a device which is simple and convenient to use.

A still further object of the invention is to provide a more sophisticated measurement technique to select optimal prosthesis size or determine if a bone receiving surface has been properly prepared for a particular prosthesis.

SUMMARY OF THE INVENTION

The present invention accomplishes all of the above objects of invention. The present invention provides a prosthetic gauge which is used for measuring a receiving bone or cartilage surface for a prosthetic device. The gauge includes a portion for gripping and a bone or cartilage contact portion extending from the gripping portion. The surface of the contact portion is predeterminedly contoured to substantially conform to the shape of the receiving cartilage or bone surface to be evaluated. The contact surface of the gauge is a frosted, diffusing surface or a translucent surface. This surface transmits and diffuses light so that the specific bone or cartilage surface being observed through the gauge cannot be seen clearly until actual contact is made between the gauge contact surface and the bone or cartilage surface. Thus, if the gauge being used to measure the articular surface corresponds or conforms well to the shape of the articular surface, the contact surface of the gauge will be fully contacting the articular surface and the articular surface will be clearly visible through the gauge. If the gauge being used to measure the bone or cartilage surface does not correspond or conform well to the shape of the articular surface, only portions of the bone or cartilage surface in contact with the gauge contact portion will be clearly visible. The present prosthetic gauge invention enhances visualization of the contact area, thus aiding the surgeon in more accurately determining the apparent contact area and hence in evaluating the potential fit of the prosthesis.

A plurality of gauges may be provided having contacting portions with dimensions that vary from one another. Each of the gauges is contoured so as to be similar to the appropriate bone or cartilage surface to be measured. When the proper size prosthesis needs to be determined, the gauges are applied, in turn, to the receiving bone or cartilage surface to evaluate the best fit. The proper size prosthesis having the best fit is then selected.

BRIEF DESCRIPTION OF THE DRAWINGS

These features and objects of the invention, as well as others, will become apparent to those skilled in the art by referring to the accompanying drawings in which.

DETAILED DESCRIPTION OF THE INVENTION

Figure 1:
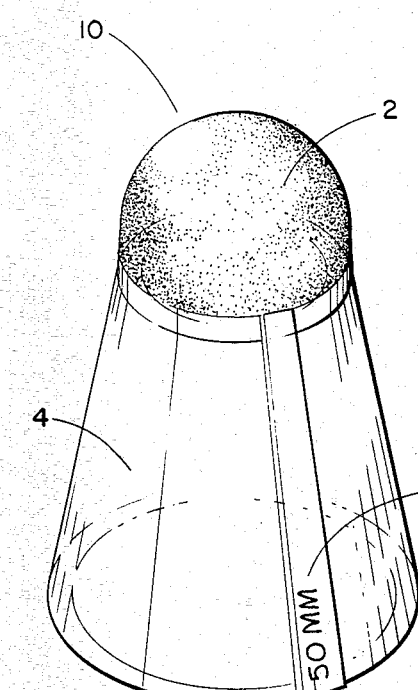
FIG. 1 is a perspective view of an acetabular gauge according to the present invention.
Figure 2:
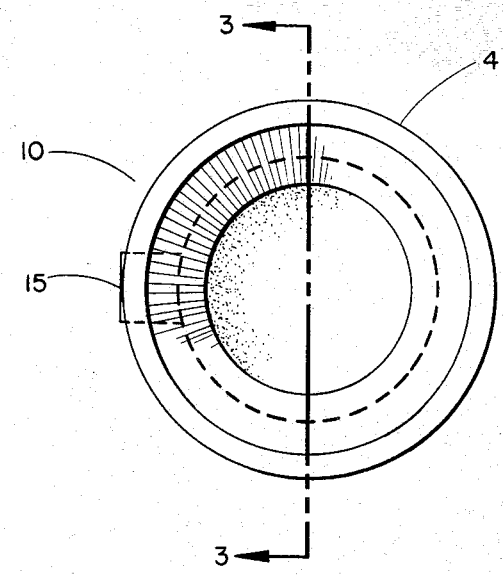
FIG. 2 is a bottom view of the gauge of FIG. 1.
Figure 3:
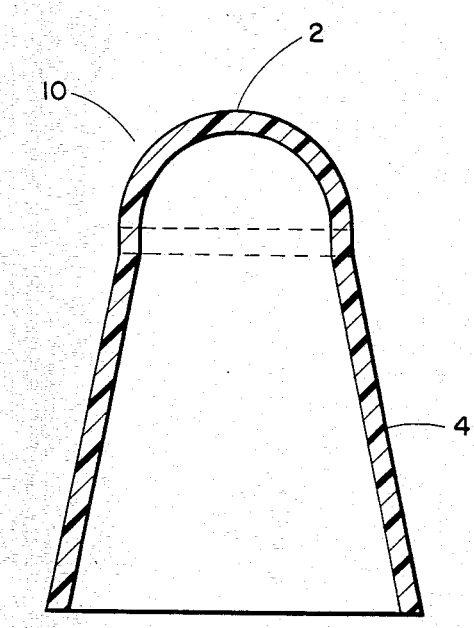
FIG. 3 is a cross-sectional view of the gauge taken along lines 3—3 of FIG. 2.
Figure 4:
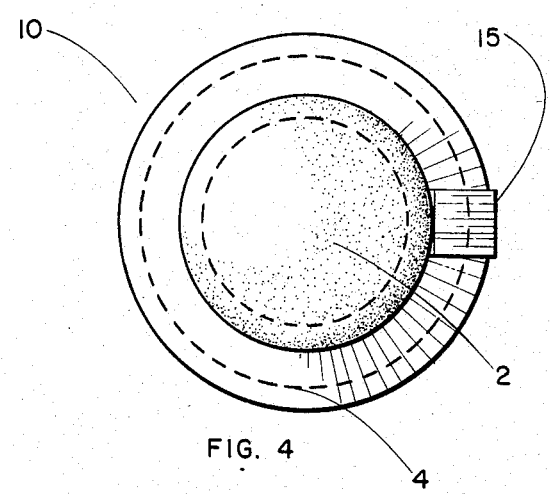
FIG. 4 is a top view of the gauge of FIG. 1.

FIGS. 1-4 illustrate a prosthetic gauge according to the present invention. These Figs. illustrate a gauge 10 which may be utilized to measure a hemispherical surface, such as an acetabular socket.

The gauge 10 includes a portion for gripping 4 and a bone or cartilage contacting surface portion 2 extending from the gripping portion 4. The contact surface 2 is predeterminedly contoured to substantially conform to the shape of the receiving cartilage or bone surface to be evaluated. For example, in the case of a hemispherical acetabulum, the coresponding cartilage contacting surface 2 is a hemispherical in shape, such as is shown in FIGS. 1-4. The gripping portion 4 may be any convenient means adapted for gripping the gauge for use. The gauge 10 illustrated in FIGS. 1-4 utilizes an open-ended skirt-shaped rim which conically extends from the contact surface 2. This skirt-shaped gripping portion 4 may be easily grasped for use as a handle for the gauge. This open-ended gripping portion 4 advantageously tapers outward from the contact surface 2 to allow the contact surface 2 to be easily viewed through the skirt portion. Other suitable gripping portions could be utilized with the contact surface 2 of the acetabular gauge 10.

The bone or cartilage contact surface 2 is translucent to enhance the optical characteristics of the material. This translucent surface transmits and diffuses light so that the specific bone or cartilage surface being observed through the contact surface 2 cannot be seen clearly until actual contact is made between the gauge contact surface 2 and the receiving bone or cartilage surface. This translucent surface may be achieved by adding a frosty surface to an otherwise clear or transparent contact surface 2.

A particularly advantageous means of obtaining such a translucent surface is to mold a surface texture directly into the gauge contact surface 2. This may be done by manufacturing a suitable metal mold cavity designed to mold the desired shaped gauge in one piece. A surface texture is applied to the metal mold at the portion which will form the translucent surface of the gauge 10. Such metal molds may be engraved by an engraver, such as Rawal Engraver's, Inc. of Chicago, Ill. A range of textures and patterns may be used, although a particularly advantageous texture is preferably in the range of Pattern No. RE 6623 to No. RE 6624 of Raywold's. The metal mold is then used to mold the gauge 10 causing a surface texturing to be molded directly into the gauge to create the desirable translucent surface. A particularly suitable material for use when molding such a surface texture into the gauge is polymethylpentene. This material is biologically inert and is autoclavable.

Other means of creating a suitable translucent contact surface 2 may be used, such as salt or sand blasting or etching of a clear surface to produce the desired translucent effect. Also, the gauge 10 may be made of other suitable materials, such as polycarbonate or polysulfone.

While the gauge 10 is preferably molded in one piece, other suitable manufacturing methods may be used. When the gauge 10 is molded, a gate such as ridge 15 may result as shown in FIG. 1. The contact surface 2 and gripping portion 4 could also be manufactured separately in two or more pieces, and then joined by a suitable joining means. The thickness of the translucent contact surface 2 is preferably ⅛ in. 3.2 mm. Preferably, the thickness is at least 3/32 in. 2.4 mm, but not greater than about ⅛ in. (0.32 mm) for optimal visual characteristics.

The gripping portion 4 may be either transparent, translucent or opaque, as long as the contact surface 2 is viewable by the user. The open ended skirt-type gripping portion 4 of the acetabular gauge 10 of FIGS. 1-4 enables the viewer to observe through the open-ended skirt to the translucent contact surface 2.

The acetabular gauges 10 can be made in a variety of sizes to accommodate varying diameters of acetabula. Preferably, a separate size gauge is available for each size of available prosthesis. Measurements are made by applying a gauge or gauges, in turn, to the acetabulum. Two important parameters are assessed with the application of the gauges; namely, the diameter of the acetabulum and the apparent contact area on the articular cartilage. While viewing through the translucent contact surface 2, if the gauge size being used to measure the cartilage surface conforms well to the shape of the articular cartilage surface area, the contact surface of the gauge will be substantially fully contacting the articular surface, and the articular surface in contact with the gauge contact surface 2 will be fully visible through the translucent contact surface 2. Prior to making contact, the articular surface would not be clearly visible because the translucent surface diffuses the light so that objects beyond cannot be seen clearly. If the gauge is positioned against the acetabulum and the gauge does not conform well to the shape of the articular surface, only portions of the gauge contact surface 2 may actually be in contact with the articular surface. Those articular portions in contact would be clearly visible through the gauge contact surface 2, but those not in actual contact would appear hazy to the observer.

For example, if an acetabular gauge 10 is applied which is too small, the zenith of the acetabulum would be in contact with the gauge and clearly visible, while the outer rim of the acetabulum would not be in contact with the gauge and would not be clearly visible through the gauge. If an acetabular gauge 10 is applied which is too big, the rim of the acetabulum will be in contact with a portion of the gauge contact surface and hence clearly visible through that surface, but the zenith of the acetabulum would not be in contact with the gauge contact surface 2 and would therefore not be clearly visible through the gauge. When the proper gauge size is applied, substantially all the acetabular articular surface should be contacting the gauge contact surface 2.

Based on the observations from use of the translucent gauge contact surface 2, the proper prosthesis size is selected corresponding to the gauge 10 which exhibited the best contact area between the gauge and acetabular articular surface. The remainder of the surgical procedure is then performed.

It is noted that descriptive information, such as gauge size or other identification information 17, may be hot stamped or otherwise marked on the gauge 10. This information 17 may conveniently be marked along the ridge 15. The size information could then correlate to the appropriate size prosthetic device which corrsponds to the gauge. For example, information 17 indicates that the gauge shown has a 50 mm outside diameter.

While the invention has been described above with reference to an acetabular gauge, it is understood that the principles of the present invention can be applied to any suitable prosthetic gauge. A concave hemispherical, translucent contact surface could be used to measure the femoral head size. Also, if a surface replacement shell is being put on the femoral head instead of the stemmed hipped prosthesis, the head of the hip is typically contoured to accept a cap-type shell whose inner-cup surface is to correspond to the contoured shape of the femoral head. Therefore, gauges corresponding to the contoured shapes, having an appropriate translucent contact surface could be used to aid the surgeon in checking to see if this receiving bone or cartilage surface has been appropriately contoured.

Figure 5:
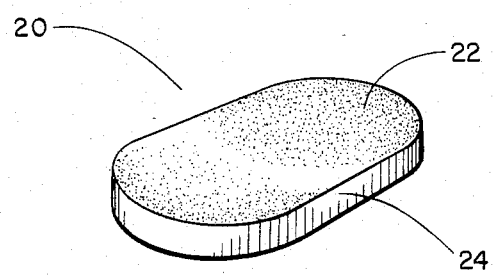
FIG. 5 is a perspective view of a tibial gauge according to the present invention.
Figure 6:
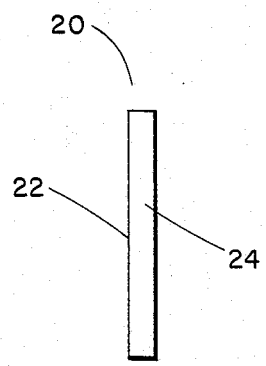
FIG. 6 is a side view of the gauge of FIG. 5.

A tibial gauge 20, according to the present invention is illustrated in FIGS. 5–6, and can be used to evaluate the fit of a tibial prosthesis prior to knee arthroplasty. The tibial gauge 20 includes a gripping portion 24 and a bone contacting surface 22 extending from the gripping portion 24. Again, the contact surface 22 is adapted to correspond to the contour of the receiving bone surface area to be measured. The receiving tibial bone surface is typically prepared to correspond to the shape of the portion of the tibial prosthesis which will be in contact with the bone. The tibial gauge 20 illustrated in FIGS. 5–6 is a flat translucent gauge. The bone contacting surface 22 is a flat surface and is translucent, such as the previously described translucent bone contacting surface of the acetabular gauge 10. The flat platformed tibial gauge 20 has a thickness to it, creating a side perimeter rim which serves as the gripping portion 24. As with the acetabular gauge 10, the thickness of the tibial gauge is preferably between about 3/32 in. 2.4 mm and ⅛ in. 3.2 mm for optimal visual characteristics for viewing the bone contact through the translucent bone contact surface 22.

This type of tibial gauge 20 is especially useful for use with a tibial prosthesis which is adapted for bone ingrowth with a porous bone ingrowth material on the bottom side of the tibial prosthesis which is to be in contact with the tibial bone surface. The gauge 20 aids in determining if the bone receiving surface has been properly prepared for a particular prosthesis. For example, the tibial bone may be cut and/or contoured to provide the flat tibial surface to correspond to a flat-bottomed tibial component. The gauge 20 can be used to ensure that the tibial surface is flat to correspond to the flat-bottomed tibial component. The translucent gauge is applied to the tibial surface and, for example, if an irregular raised portion exists on the prepared tibial surface, the gauge will rest on the raised portion, and the raised portion will be visible through the gauge 20. Any lower portions not in contact with the gauge 20 will not be visible through the translucent surface 22 of gauge 20. This would indicate to the surgeon that more contouring is needed to flatten the tibial bone surface to achieve good contact area between the bottom surface of the tibial prosthesis and the receiving tibial bone surface.

The invention described herein is a prosthetic gauge for measuring a bone or cartilage surface in order to more accurately evaluate the fit of a prosthesis. The gauge utilizes a translucent bone contact surface to enhance the optical characteristics of the gauge for determining good contact area between a prosthesis and receiving bone surface. While this invention has been described and exemplified in terms of a particularly advantageous embodiment, those skilled in the art can appreciate that modifications can be made without departing from the spirit and scope of this invention.

We claim:

1. A prosthetic gauge used for evaluating the fit of a prosthetic device against a receiving bone or cartilage surface comprising:
    a means for gripping; and
    a contact portion extending from said gripping means, said contact portion having a translucent surface, and wherein said contact portion is contoured to correspond to the surface of the prosthetic device which is to mate with the receiving bone or cartilage surface being evaluated.

2. A prosthetic gauge for evaluating the fit of a prosthetic device with respect to a receiving bone or cartilage surface comprising:

a means for gripping; and contact surface extending from said gripping means, said contact surface being substantially translucent for obscuring the visualization of said bone or cartilage surface through said contact surface when said contact surface is not in contact with said bone or cartilage surface and for clarifying the visualization of said bone or cartilage surface through said contact surface upon contact of said contact surface with said bone or cartilage surface, and wherein said contact surface is contoured to correspond to the surface of the prosthetic device which is to mate with the receiving bone or cartilage surface being evaluated.

3. The gauge of claim 2, wherein said contact surface includes a frosted surface.

4. The gauge of claim 2, wherein the translucent surface is created by a surface texturing molded directly into the gauge.

5. The gauge of claim 2, wherein descriptive information regarding the gauge is marked onto the gauge for ease of identification.

6. The gauge of claim 2 wherein said gauge is an acetabular gauge.

7. The gauge of claim 6 wherein said contact surface is substantially hemispherical and said gripping means is an open-ended skirt extending therefrom.

8. The gauge of claim 2 wherein said contact surface is substantially hemispherical and said gripping means is an open-ended skirt extending therefrom.

9. The gauge of claim 2 wherein a plurality of such gauges is provided, wherein the dimensions of the contact surface of each gauge vary incrementally from one another to enable the optimum-fit prosthesis to be selected.

* * * * *